United States Patent
Kunis

(10) Patent No.: US 8,986,248 B2
(45) Date of Patent: Mar. 24, 2015

(54) CUTTING BALLOON AND PROCESS

(75) Inventor: Christopher Kunis, Escondido, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 195 days.

(21) Appl. No.: 13/150,944

(22) Filed: Jun. 1, 2011

(65) Prior Publication Data

US 2011/0230818 A1    Sep. 22, 2011

Related U.S. Application Data

(63) Continuation of application No. 10/879,894, filed on Jun. 23, 2004, now Pat. No. 7,976,557.

(51) Int. Cl.
| | | |
|---|---|---|
| *A61B 17/22* | (2006.01) | |
| *A61D 1/02* | (2006.01) | |
| *A61M 31/00* | (2006.01) | |
| *A61M 37/00* | (2006.01) | |
| *A61M 25/10* | (2013.01) | |

(52) U.S. Cl.
CPC ....... *A61M 25/104* (2013.01); *A61M 2025/105* (2013.01); *A61M 2025/1086* (2013.01); *A61M 2025/109* (2013.01); *A61M 25/10* (2013.01); *A61M 25/1027* (2013.01); *A61M 25/1038* (2013.01); *A61M 2025/1031* (2013.01)
USPC .................. 604/103.08; 606/159; 604/103.02

(58) Field of Classification Search
CPC ..................... A61M 25/104; A61M 2025/105; A61M 2025/1086; A61M 2025/109
USPC ...................... 604/22, 96.01, 103.08, 103.09; 606/159, 167, 170
See application file for complete search history.

(56) References Cited

U.S. PATENT DOCUMENTS

| | | | |
|---|---|---|---|
| 4,030,503 A | 6/1977 | Clark, III et al. | |
| 4,273,128 A | 6/1981 | Lary | |
| 4,669,469 A | 6/1987 | Gifford et al. | |
| 4,696,667 A | 9/1987 | Masch | |
| 4,728,319 A | 3/1988 | Masch | |
| 4,781,186 A | 11/1988 | Simpson et al. | |
| 4,784,636 A | 11/1988 | Rydell | |
| 4,787,388 A | 11/1988 | Hofmann | |
| 4,867,157 A | 9/1989 | McGurk-Burleson et al. | |
| 4,886,061 A | 12/1989 | Fischell | |
| 4,887,613 A | 12/1989 | Farr et al. | |
| 4,896,669 A | 1/1990 | Bhate et al. | |
| 4,909,781 A | 3/1990 | Husted | |

(Continued)

FOREIGN PATENT DOCUMENTS

| | | |
|---|---|---|
| EP | 533511 A1 | 3/1993 |
| EP | 565799 B1 | 8/1996 |

(Continued)

OTHER PUBLICATIONS

U.S. Appl. No. 09/696,378, filed Oct. 25, 2000, Chen et al.

*Primary Examiner* — Nathan R Price
(74) *Attorney, Agent, or Firm* — Seager, Tufte & Wickhem, LLC

(57) ABSTRACT

A method of preparing a cutting balloon comprises the steps of providing a balloon body having an exterior surface, an unexpanded state and an expanded state; and engaging at least one blade to the exterior surface when the balloon body is in the unexpanded state.

8 Claims, 4 Drawing Sheets

(56) References Cited

U.S. PATENT DOCUMENTS

| | | |
|---|---|---|
| 4,950,277 A | 8/1990 | Farr |
| 4,963,313 A | 10/1990 | Noddin et al. |
| 4,966,604 A | 10/1990 | Reiss |
| 4,979,951 A | 12/1990 | Simpson |
| 4,986,807 A | 1/1991 | Farr |
| 5,030,201 A | 7/1991 | Palestrant |
| 5,053,044 A | 10/1991 | Mueller et al. |
| 5,074,871 A | 12/1991 | Groshong |
| 5,091,205 A | 2/1992 | Fan |
| 5,100,425 A | 3/1992 | Fischell |
| 5,112,900 A | 5/1992 | Buddenhagen et al. |
| 5,146,395 A | 9/1992 | McKie et al. |
| 5,156,610 A | 10/1992 | Reger |
| 5,176,693 A | 1/1993 | Pannek |
| 5,178,625 A | 1/1993 | Groshong |
| 5,181,920 A | 1/1993 | Mueller et al. |
| 5,192,291 A | 3/1993 | Pannek |
| 5,196,024 A | 3/1993 | Barath |
| 5,209,749 A | 5/1993 | Buelna |
| 5,217,474 A | 6/1993 | Zacca et al. |
| 5,224,945 A | 7/1993 | Pannek |
| 5,226,887 A | 7/1993 | Farr et al. |
| 5,226,909 A | 7/1993 | Evans et al. |
| 5,250,059 A | 10/1993 | Andreas et al. |
| 5,282,484 A | 2/1994 | Reger |
| 5,308,354 A | 5/1994 | Zacca et al. |
| 5,312,427 A | 5/1994 | Shturman |
| 5,314,438 A | 5/1994 | Shturman et al. |
| 5,320,634 A | 6/1994 | Vigil |
| 5,356,418 A | 10/1994 | Shturman |
| 5,372,601 A | 12/1994 | Lary |
| 5,395,377 A | 3/1995 | Petersen |
| 5,431,673 A | 7/1995 | Summers et al. |
| 5,443,443 A | 8/1995 | Shiber et al. |
| 5,447,497 A | 9/1995 | Sogard et al. |
| 5,527,325 A | 6/1996 | Conley et al. |
| 5,556,408 A | 9/1996 | Farhat |
| 5,616,149 A | 4/1997 | Barath |
| 5,622,188 A | 4/1997 | Plaia et al. |
| 5,632,755 A | 5/1997 | Nordgren et al. |
| 5,669,920 A | 9/1997 | Conley et al. |
| 5,681,336 A | 10/1997 | Clement et al. |
| 5,697,944 A | 12/1997 | Lary |
| 5,713,913 A | 2/1998 | Lary |
| 5,718,684 A | 2/1998 | Gupta |
| 5,728,123 A | 3/1998 | Lemelson |
| 5,728,129 A | 3/1998 | Summers et al. |
| 5,766,203 A | 6/1998 | Imran et al. |
| 5,792,158 A | 8/1998 | Lary |
| 5,797,935 A | 8/1998 | Barath |
| 5,800,450 A | 9/1998 | Lary |
| 5,833,657 A | 11/1998 | Reinhardt et al. |
| 5,836,868 A | 11/1998 | Ressemann et al. |
| 5,842,479 A | 12/1998 | Plaia et al. |
| 5,843,103 A | 12/1998 | Wulfman et al. |
| 5,882,329 A | 3/1999 | Patterson et al. |
| 5,897,567 A | 4/1999 | Ressemann et al. |
| 5,902,263 A | 5/1999 | Patterson et al. |
| 5,941,869 A | 8/1999 | Patterson et al. |
| 5,949,200 A | 9/1999 | Ference et al. |
| 5,968,013 A | 10/1999 | Smith et al. |
| 6,001,112 A | 12/1999 | Taylor |
| 6,015,420 A | 1/2000 | Wulfman et al. |
| 6,036,708 A | 3/2000 | Sciver |
| 6,090,135 A | 7/2000 | Plaia et al. |
| 6,096,054 A | 8/2000 | Wyzgala et al. |
| 6,102,908 A | 8/2000 | Tu et al. |
| 6,117,153 A | 9/2000 | Lary et al. |
| 6,124,007 A | 9/2000 | Wang et al. |
| 6,129,706 A | 10/2000 | Janacek |
| 6,146,395 A | 11/2000 | Kanz et al. |
| 6,156,046 A | 12/2000 | Passafaro et al. |
| 6,165,187 A | 12/2000 | Reger |
| 6,183,487 B1 | 2/2001 | Barry et al. |
| 6,197,013 B1 | 3/2001 | Reed et al. |
| 6,245,040 B1 | 6/2001 | Inderbitzen et al. |
| 6,245,050 B1 | 6/2001 | Odorzynski et al. |
| 6,258,108 B1 | 7/2001 | Lary |
| 6,270,509 B1 | 8/2001 | Barry et al. |
| 6,306,151 B1 | 10/2001 | Lary |
| 6,319,242 B1 | 11/2001 | Patterson et al. |
| 6,328,750 B1 | 12/2001 | Berry et al. |
| 6,398,798 B2 | 6/2002 | Selmon et al. |
| 6,406,523 B1 | 6/2002 | Connor et al. |
| 6,428,552 B1 | 8/2002 | Sparks |
| 6,482,216 B1 | 11/2002 | Hiblar et al. |
| 6,500,186 B2 | 12/2002 | Lafontaine et al. |
| 6,517,514 B1 | 2/2003 | Campbell |
| 6,562,062 B2 | 5/2003 | Jenusaitis et al. |
| 6,565,527 B1 | 5/2003 | Jonkman |
| 6,632,231 B2 | 10/2003 | Radisch, Jr. |
| 6,652,548 B2 | 11/2003 | Evans et al. |
| 6,685,718 B1 | 2/2004 | Wyzgala et al. |
| 6,730,105 B2 | 5/2004 | Shiber |
| 6,746,463 B1 | 6/2004 | Schwartz |
| 6,808,531 B2 | 10/2004 | LaFontaine et al. |
| 6,951,566 B2 | 10/2005 | Lary |
| 7,030,503 B2 | 4/2006 | Ohnishi et al. |
| 7,153,315 B2 | 12/2006 | Miller |
| 7,172,609 B2 | 2/2007 | Radisch, Jr. |
| 7,279,002 B2 * | 10/2007 | Shaw et al. ............ 623/1.11 |
| 7,291,158 B2 | 11/2007 | Crow et al. |
| 7,314,480 B2 | 1/2008 | Eidenschink et al. |
| 7,329,267 B2 | 2/2008 | Weber |
| 7,338,463 B2 | 3/2008 | Vigil |
| 7,393,397 B2 | 7/2008 | Ham |
| 7,413,558 B2 | 8/2008 | Kelley et al. |
| 7,494,497 B2 | 2/2009 | Weber |
| 7,566,319 B2 | 7/2009 | McAuley et al. |
| 7,632,288 B2 | 12/2009 | Wu |
| 7,658,744 B2 * | 2/2010 | Jackson ................ 606/159 |
| 7,736,375 B2 | 6/2010 | Crow |
| 7,753,907 B2 | 7/2010 | DiMatteo et al. |
| 7,754,047 B2 | 7/2010 | Kelley |
| 7,758,604 B2 | 7/2010 | Wu et al. |
| 7,799,043 B2 | 9/2010 | O'Brien et al. |
| 7,879,053 B2 | 2/2011 | Trinidad |
| 7,887,557 B2 | 2/2011 | Kelley et al. |
| 7,985,234 B2 | 7/2011 | Wang et al. |
| 8,038,691 B2 | 10/2011 | Bence et al. |
| 8,043,259 B2 | 10/2011 | Radisch, Jr. et al. |
| 8,043,311 B2 | 10/2011 | Radisch, Jr. et al. |
| 8,048,093 B2 | 11/2011 | Mapes et al. |
| 8,066,726 B2 | 11/2011 | Kelley |
| 2002/0010489 A1 | 1/2002 | Grayzel et al. |
| 2002/0016624 A1 | 2/2002 | Patterson et al. |
| 2002/0029015 A1 | 3/2002 | Camenzind et al. |
| 2002/0151924 A1 | 10/2002 | Shiber |
| 2003/0078606 A1 | 4/2003 | Lafontaine et al. |
| 2003/0144677 A1 | 7/2003 | Lary |
| 2003/0163148 A1 | 8/2003 | Wang et al. |
| 2003/0229370 A1 * | 12/2003 | Miller ................ 606/159 |
| 2004/0122457 A1 | 6/2004 | Weber |
| 2004/0127920 A1 | 7/2004 | Radisch, Jr. |
| 2004/0225347 A1 * | 11/2004 | Lang ................ 623/1.15 |
| 2005/0288629 A1 | 12/2005 | Kunis |
| 2006/0111736 A1 | 5/2006 | Kelley |
| 2006/0129093 A1 | 6/2006 | Jackson |
| 2006/0135980 A1 | 6/2006 | Trinidad |
| 2006/0259005 A1 | 11/2006 | Konstantino et al. |

FOREIGN PATENT DOCUMENTS

| | | |
|---|---|---|
| WO | 9923958 A1 | 5/1999 |
| WO | 0187372 A1 | 11/2001 |

\* cited by examiner

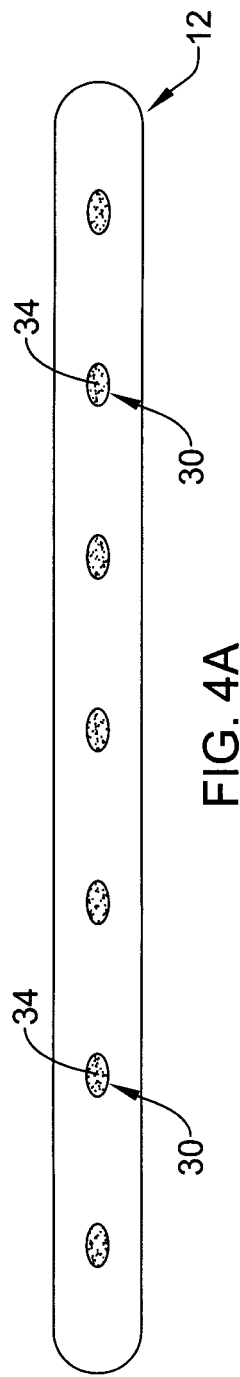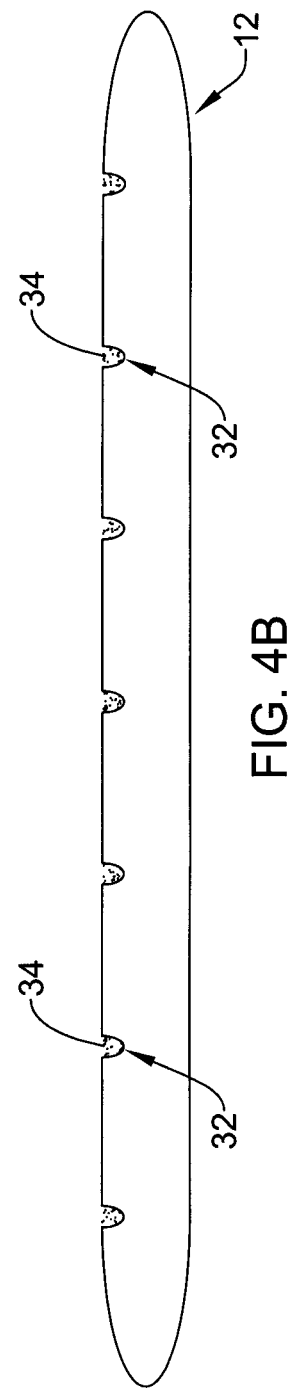

CUTTING BALLOON AND PROCESS

CROSS-REFERENCE TO RELATED APPLICATIONS

This application is a continuation of U.S. patent application Ser. No. 10/879,894, now U.S. Pat. No. 7,976,557, filed on Jun. 23, 2004, the entire disclosure of which is incorporated herein by reference.

BACKGROUND

Arterial blockages, which are also called stenoses, are typically caused by the build-up of atherosclerotic plaque on the inside wall of an artery. In fact, several such stenoses may occur contiguously within a single artery. This can result in a partial, or even complete, blockage of the artery. As a result of the danger associated with such a blockage, several methods and procedures have been developed to treat stenoses. One such method is an angioplasty procedure which uses an inflatable balloon to dilate the blocked artery. A typical inflatable angioplasty device, for example, is disclosed in U.S. Pat. No. 4,896,669.

Angioplasty balloons have enjoyed widespread acceptance in the treatment of stenoses. Recent studies, however, have indicated that the efficacy of the dilation of a stenosis is enhanced by first, or simultaneously, incising the material that is creating the stenosis. Consequently, recent developments have been made to equip angioplasty balloons with cutting edges, or atherotomes, which are intended to incise a stenosis during the dilation procedure. For example, U.S. Pat. No. 5,196,024; U.S. Pat. No. 5,616,149 and U.S. Pat. No. 5,797,935 respectively describe an inflatable angioplasty balloon having a number of atherotomes mounted longitudinally on the surface of the balloon. Upon inflation of the balloon, the atherotomes induce a series of longitudinal cuts into the surface of the stenotic material as the balloon expands to dilate the stenosis. As a result of such cuts, the stenosis is more easily dilated, and the likelihood of damaging the artery during dilation is reduced.

In manufacturing a balloon having one or more atherotomes or blades, typically the balloon is inflated and one or more blades are bonded to the balloon while it remains inflated. The necessity of inflating the balloon in order to position the blades thereon is time consuming and can lead to additional manufacturing complications as it may be difficult to position the blades with sufficient accuracy so as maintain a reduced balloon profile and to minimize interference of the blades with the folds of the balloon when it is uninflated and loaded onto a catheter for use.

In light of the above it would be desirable to provide a balloon and method of manufacturing the same, which presents a balloon having one or more blades wherein a blade is placed on the balloon body without the necessity of having to first inflate the balloon.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description below.

A brief abstract of the technical disclosure in the specification is provided as well only for the purposes of complying with 37 C.F.R. 1.72. The abstract is not intended to be used for interpreting the scope of the claims.

BRIEF SUMMARY

The present invention is directed to several embodiments. In at least one embodiment the invention is directed to a medical balloon for use with a catheter or similar device, wherein the medical balloon is equipped with at least one cutting blade.

In some embodiments, the balloon may be configured for use in conjunction with an implantable medical prosthesis such a stent, graft, stent-graft, vena cava filter, or other similar device hereinafter collectively referred to as stents.

In at least one embodiment at least one blade is positioned on the outer surface of the balloon. In some embodiments, when the balloon is expanded the at least one blade defines a substantially spiral-like path about the balloon body. In some embodiments, when the balloon is deflated the at least one blade defines a substantially straight path along the balloon body. In some embodiments, when the balloon is folded into a reduced profile configuration for passage into a lumen, the at least one blade is substantially parallel to the longitudinal axis of the catheter.

In at least one embodiment the invention is directed to a method of manufacturing a medical balloon having at least one blade positioned thereon, wherein the at least one blade is positioned on the balloon without having to inflate the balloon.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

FIGS. 4A and 4B are detailed perspective views of the blade shown in FIGS. 1-3.

DETAILED DESCRIPTION

Figure 1:
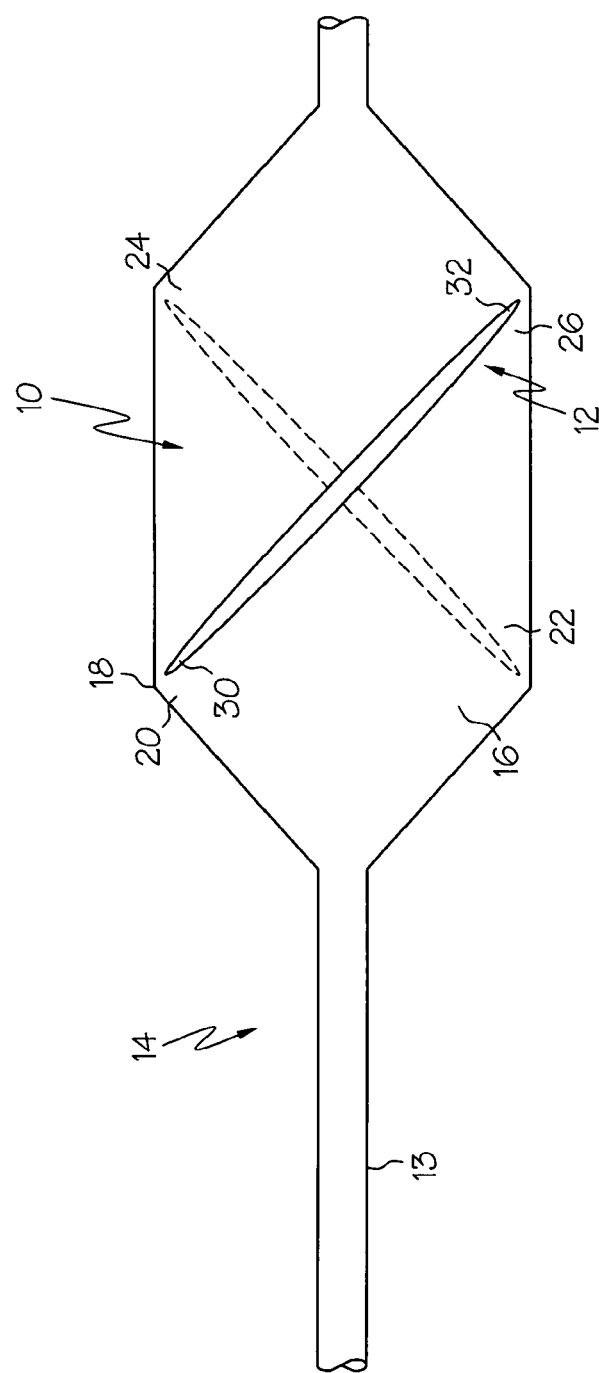
FIG. 1 is a side view of an embodiment of the invention wherein the balloon is shown in an unexpanded state.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 2:
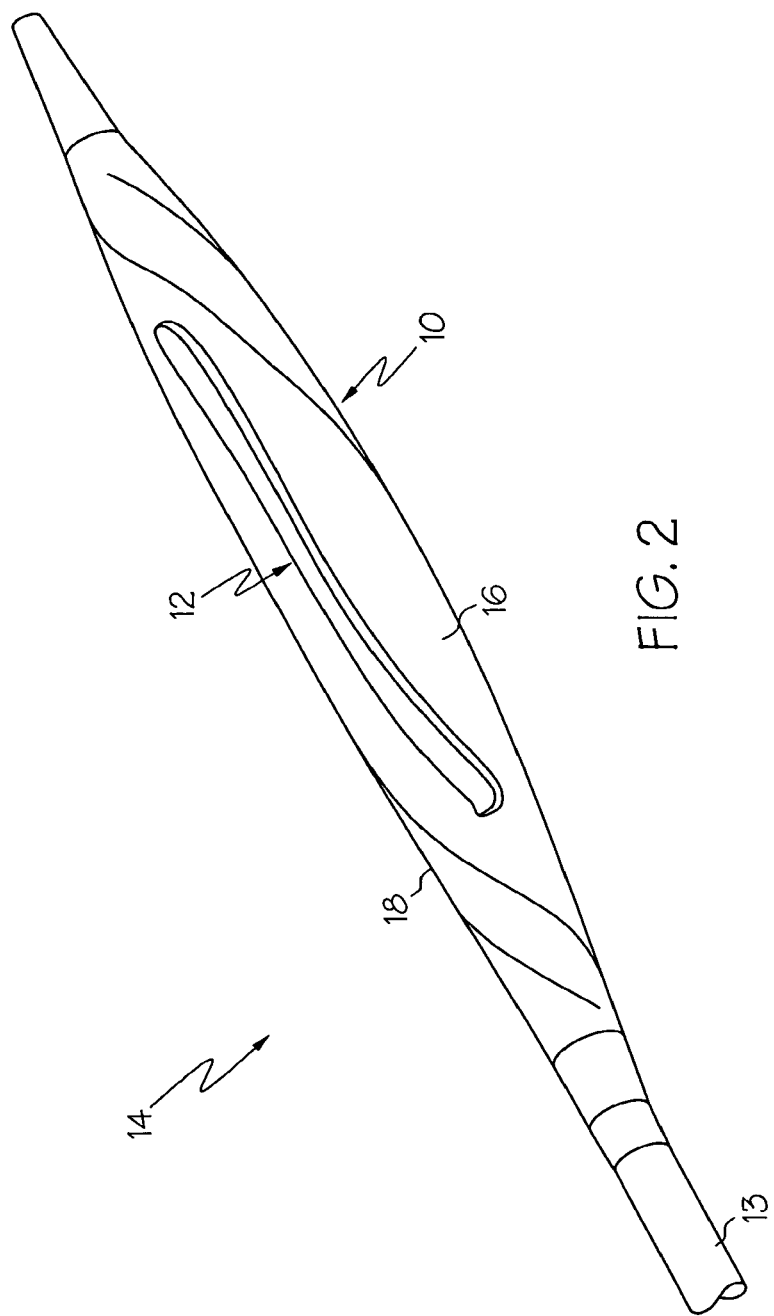
FIG. 2 is a perspective view of the embodiment shown in FIG. 1 wherein the balloon is shown in a folded configuration.
Figure 3:
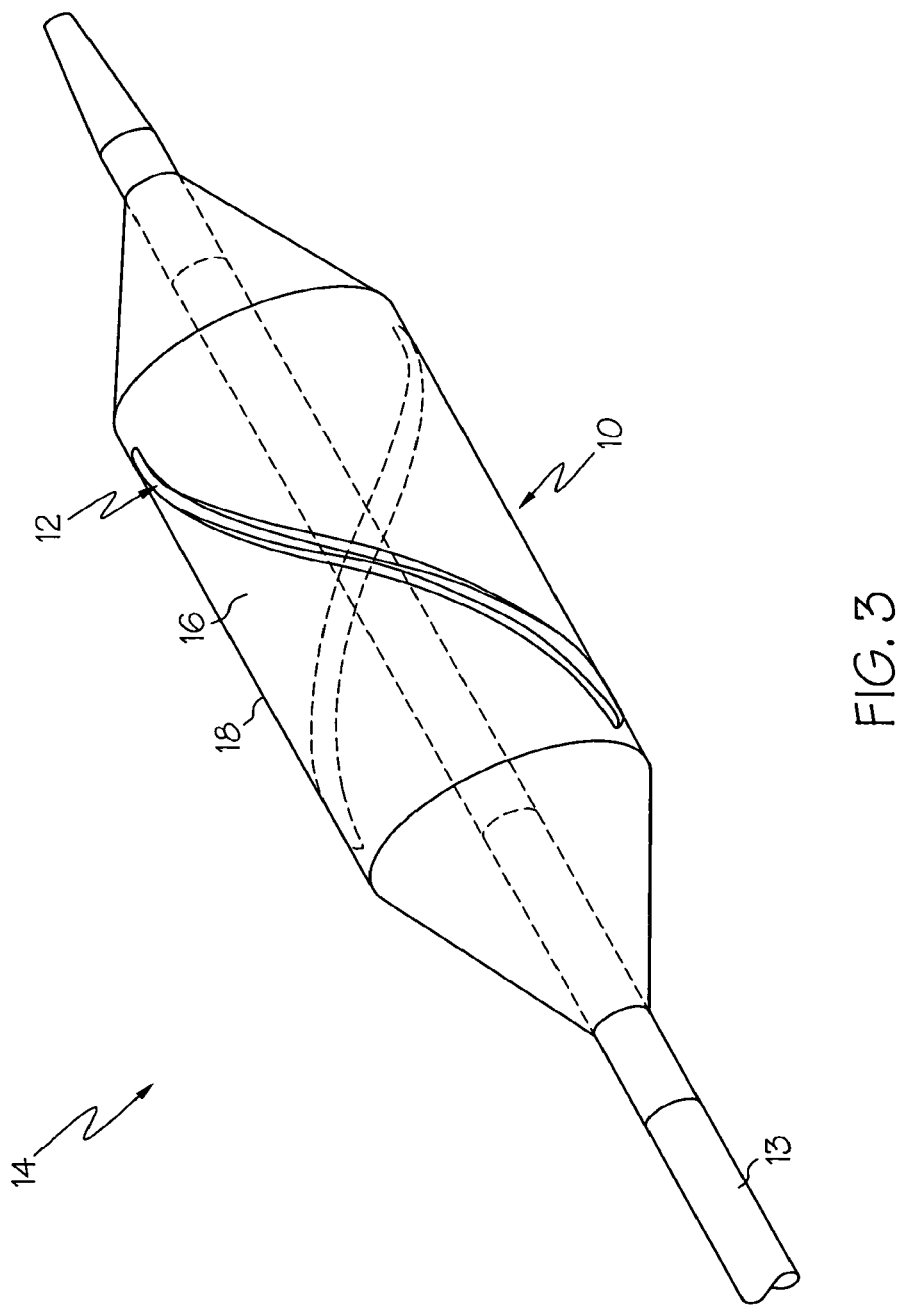
FIG. 3 is a perspective view of the embodiment shown in FIG. 2 wherein the balloon is shown in an expanded state.

As indicated above, the present invention is embodied in a variety of forms. In at least one embodiment, an example of which is illustrated in FIGS. 1-3, the invention is directed to a balloon 10 for use with a catheter 14, wherein the balloon 10 is equipped with at least one atherotome, cutting member or blade 12. In the embodiment shown, a blade 12 is positioned on the exterior surface 16 of the balloon body 18 so that when the balloon 10 is expanded, such as in the manner shown in FIG. 3, the blade 12 defines a substantially spiral-like or helical path about the circumference of the balloon body 18. A blade 12 is engaged to the balloon 10 when the balloon 10 is in a deflated, flattened out state, such as is depicted in FIG. 1.

While there are many ways to engage a blade to a balloon body, such as the prior art method discussed above, which requires that the balloon body be expanded in order to position the blade thereon, in at least one embodiment of the present invention, the invention is directed to a method wherein a blade 12 is engaged to the exterior surface 16 of the balloon body 18, while the balloon body is in an unexpanded, flattened out state. Not only does this new method save time and money, it provides a more simplified mechanism for engaging a blade 12 to the balloon body 18.

In at least one embodiment, after the balloon body 18 has been formed such as by extrusion, molding, etc., one or more blades 12, is engaged to the exterior surface 16 of the balloon 10 using any engagement method desired. For example, in some embodiments a blade 12 may by engaged to the balloon body 18 such as by adhesive engagement, mechanical engagement, etc. In at least one embodiment the blade 12 may be mechanically engaged to the balloon body 18 such as by providing the blade 12 and the exterior surface 16 of the balloon body 18 with one or more interlocking surface features for mutual securement. In at least one embodiment a chemical adhesive is applied to one or both of the balloon body 18 and the blade 12 to adhesively engage one to the other. Other mechanisms for engaging blade 12 to the balloon body 18 may also be utilized.

The balloon body 18 may be made of any suitable balloon material including compliant and non-compliant materials and combinations thereof. Some examples of suitable materials for constructing the balloon body 18 include but are not limited to: low pressure, relatively soft or flexible polymeric materials, such as thermoplastic polymers, thermoplastic elastomers, polyethylene (high density, low density, intermediate density, linear low density), various co-polymers and blends of polyethylene, ionomers, polyesters, polyurethanes, polycarbonates, polyamides, poly-vinyl chloride, acrylonitrile-butadiene-styrene copolymers, polyether-polyester copolymers, and polyetherpolyamide copolymers; copolymer polyolefin material available from E.I. DuPont de Nemours and Co. (Wilmington, Del.), under the trade name Surlyn™; ionomer and a polyether block amide available under the trade name PEBAX™; high pressure polymeric materials, such as thermoplastic polymers and thermoset polymeric materials, polyethylene terephthalate) (commonly referred to as PET), polyimide, thermoplastic polyamide, polyamides, polyesters, polycarbonates, polyphenylene sulfides, polypropylene and rigid polyurethane; one or more liquid crystal polymers; and combinations of one or more of any of the above.

Blade 12 may be constructed from one or more metals, polymers, combinations of one or more metals and/or polymers, and/or other desired material(s). In at least one embodiment, blade 12 is at least partially constructed of a shape memory material, such as nitinol and/or a shape memory polymer. The blade 12 may comprise a plurality of separate blade segments or may be a single continuous structure as desired.

As may be seen in FIG. 1, a convenient aspect of affixing blade 12 to balloon body 18 in the unexpanded state is that the blade 12 may be engaged to the balloon body 18 while the blade 12 is in a substantially linear configuration and the balloon 10 is substantially flattened out or "pancaked". In at least one embodiment, the blade 12 is substantially straight when it is engaged to the exterior surface 16 of the flattened balloon body 18. That is to say, it is not necessary to provide the blade 12 with one or more bends or curves (such as would be necessary when affixing a blade to a balloon in the expanded state) when the blade 12 is engaged to the exterior surface 16 of the balloon body 18, unless such features are desired.

In at least one embodiment, when the balloon body 18 is in the unexpanded "flattened" state the exterior surface 16 of the balloon body 18 comprises four corner regions. This is true even in the case of a substantially cylindrical shaped balloon when it is flattened in the unexpanded state. The corner regions may be described by their respective orientation such as: a proximal top corner 20, a proximal bottom corner 22, a distal top corner 24 and a distal bottom corner 26.

In order to provide the balloon 10 with a blade 12 having a substantially spiral-like configuration in the expanded state, such as is shown in FIG. 3, the blade 12 is engaged to the balloon body 18 in the unexpanded state so that the ends 30 and 32 of the blade 12 are positioned in opposite corner regions such as in the manner shown in FIG. 1. For example, an end of the blade 12 may be positioned in the proximal top corner 20 while the other end is positioned in the distal bottom corner 26 of the unexpanded balloon body 18. In some embodiments a blade end is be positioned in the proximal bottom corner 22 and the other blade end is positioned in the distal top corner 24.

If desired, the blade 12 may be positioned in any manner desired upon the balloon body 18. The opposing corner to corner, substantially linear configuration of the balloon 10 shown in FIG. 1 is an embodiment which will provide the substantially spiral-like blade orientation shown in FIG. 3. It is recognized that other configurations may be desired, such as for example, a blade 12 may be engaged to the balloon body 18 so that in the expanded state the balloon 10 is provided with a blade or blades 12 that are substantially longitudinally disposed, radially disposed or otherwise positioned or disposed about the balloon body 18. As such, a blade 12 may be engaged to the balloon body 18 in the unexpanded state with any orientation in order to provide the balloon 10 in the expanded state with a blade 12 that has any configuration desired.

Where the balloon 10 is produced separately from the shaft 13 of the catheter 14, the blade 12 may be engaged to the balloon body 18 before or after the balloon 10 is affixed to the catheter shaft 13.

Once blade 12 is engaged to the balloon body 18, and the balloon 10 is engaged to the catheter shaft 13, the unexpanded balloon 10 is folded and/or wrapped, such as in the manner shown in FIG. 2 in order to attain a reduced profile configuration suitable for advancement within a body lumen or vessel.

In some embodiments the catheter 14 may be configured to deliver one or more therapeutic agents to a stenosis, aneurysm or lesion within a body lumen. In some embodiments at least a portion of the blade 12 is configured to include one or more holes 30, notches 32, or other surface features for use in delivering one or more therapeutic agents 34 to a lesion, as seen in FIGS. 4A and 4B, for example. A therapeutic agent may be placed on the blade 12 and/or the exterior surface 16 of the balloon body 18 in the form of one or more coatings. In at least one embodiment the coating includes at least one therapeutic agent and at least one polymer.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed:

1. A cutting balloon catheter, comprising:
    an elongate catheter shaft;
    an inflatable balloon secured to a distal end region of the catheter shaft, said inflatable balloon having a proximal tapered region, a distal tapered region and a body portion between the proximal and distal tapered regions, the body portion being cylindrical in an expanded state and adapted to be flattened in an unexpanded state;
    a plurality of cutting members disposed on an exterior surface of the balloon each cutting member of the plurality of cutting members having a first end and a second end,
    wherein the plurality of cutting members assume a linear configuration in the flattened unexpanded state with the first and second ends of each cutting member located on the body portion of the inflatable balloon,
    wherein each cutting member includes a cutting edge that defines a continuous helical path around the balloon in the expanded state; and
    a therapeutic agent disposed on the cutting members;
    wherein the cutting members include a plurality of surface characteristics formed in a surface of each of the cutting members for receiving the therapeutic agent for delivery to a treatment site.

2. The cutting balloon catheter of claim 1, wherein the cutting members are secured to the exterior surface of the balloon.

3. The cutting balloon catheter of claim 1, further comprising a coating on the exterior surface of the balloon including a therapeutic agent.

4. The cutting balloon catheter of claim 1, wherein the plurality of surface characteristics includes a plurality of holes in the surface of the cutting member.

5. The cutting balloon catheter of claim 4, wherein the therapeutic agent is disposed in the plurality of holes of the cutting member.

6. The cutting balloon catheter of claim 1, wherein the plurality of surface characteristics includes a plurality of notches in the surface of the cutting member.

7. The cutting balloon catheter of claim 6, wherein the therapeutic agent is disposed in the plurality of notches of the cutting member.

8. The cutting balloon catheter of claim 1, wherein the therapeutic agent is included in a coating on the surface of the cutting member.

* * * * *